United States Patent
Yarovoy et al.

(10) Patent No.: US 6,544,938 B1
(45) Date of Patent: Apr. 8, 2003

(54) SOAP BAR COMPRISING HIGH LEVELS OF SPECIFIC ALKOXYLATED TRIGLYCERIDES WHICH PROVIDE ENHANCED SENSORY PROPERTIES AND PROCESS WELL

(75) Inventors: Yury Yarovoy, Berkeley Heights, NJ (US); Michael Massaro, Congers, NY (US); Rajesh Patel, Lyndhurst, NJ (US)

(73) Assignee: Unilever Home & Personal Care USA, Division of Conopco, Inc., Greenwich, CT (US)

(*) Notice: Subject to any disclaimer, the term of this patent is extended or adjusted under 35 U.S.C. 154(b) by 0 days.

(21) Appl. No.: 09/969,345

(22) Filed: Oct. 2, 2001

(51) Int. Cl.[7] ................................. A61K 7/50
(52) U.S. Cl. .................. 510/153; 510/141; 510/151; 510/152; 510/155
(58) Field of Search ................ 510/141, 152, 510/153, 155, 151

(56) References Cited

U.S. PATENT DOCUMENTS

| | | |
|---|---|---|
| 3,814,698 A | 6/1974 | Ferrara et al. |
| 3,941,712 A | 3/1976 | Ferrara et al. |
| 6,242,398 B1 | 6/2001 | Chambers et al. |
| 6,255,265 B1 | 7/2001 | Van Gunst et al. |

FOREIGN PATENT DOCUMENTS

| | | |
|---|---|---|
| EP | 0586323 | 3/1994 |
| EP | 1045021 | 10/2000 |

*Primary Examiner*—Necholus Ogden
(74) *Attorney, Agent, or Firm*—Ronald A. Koatz

(57) ABSTRACT

The present invention relates to the composition comprising soap and alkoxylated triglyceride wherein said bars have improved sensory properties (e.g., reduced drag and stickiness; and enhanced slipperiness) relative to identical bar with non-alkoxylated triglyceride.

6 Claims, 1 Drawing Sheet

SOAP BAR COMPRISING HIGH LEVELS OF SPECIFIC ALKOXYLATED TRIGLYCERIDES WHICH PROVIDE ENHANCED SENSORY PROPERTIES AND PROCESS WELL

FIELD OF THE INVENTION

The present invention relates to predominately soap based bars (e.g., about 50% to 85% by wt. soap) comprising high levels (e.g., 7% to 15%, preferably 8% to 14%) of alkoxylated triglycerides. The alkoxylated triglycerides used at these levels provide excellent sensory properties (e.g., wet skin feel associated with moisturization and skin care, less "draggy" feel, creamy lather). In addition, the alkoxylated triglycerides provide acceptable to superior hardness and yield stress and thus are "readily" processable. In this regard, the alkoxylated triglycerides provide a single, inexpensive method of providing skin care benefits into simple soap base.

BACKGROUND OF THE INVENTION

Traditionally, emollient oils such as mineral oils, silicone oils, emollient esters and triglycerides have been incorporated into soap bars at relatively low levels, i.e., less than 5.0%. Higher levels have been avoided because they have been believed to cause problems in processing and in user properties (e.g., poor lather). At the low levels used, however, there is little discernible sensory effect.

In U.S. Pat. Nos. 3,814,698 and 3,941,712, both to Ferrara, compositions having much higher levels of "bath oil" are added at bar saponification step (when ingredients are liquid) rather than milling steps.

In both Ferrara patents, the bath oil is broadly defined to include materials such as oils, esters, waxes, long chain alcohols. No one material is said to work better than another and alkoxylated triglycerides specifically are certainly not disclosed. Further, as noted, materials are added at saponification step indicating the invention is clearly about processing and not about differences in composition.

U.S. Pat. No. 6,242,398 to Chambers, discloses soap, benefit agent and water. There is no specific disclosure of alkoxylated triglycerides and how these are superior to non-alkoxylated (particularly in sensory property such as much less drag). Further, emollients are applied in a carrier rather than being mixed/milled directly into final compositions.

In two of applicants' co-pending applications entitled (1) "Soap Bar Comprising About 6% and Greater Triglycerides Which Structure Well and Have Desirable User Properties"; and (2) "Process for Making Soap Bar Comprising About 6% and Greater Triglycerides", applicants disclose levels of up to 13% by wt. of triglycerides incorporated into bars at finishing stage.

There is no mention of alkoxylated triglycerides in these applications. Moreover, applicants have found that the alkoxylated triglycerides structure better than unmodified triglycerides into bars, can be incorporated at higher levels (e.g., up to 15% by wt.) and provide enhanced sensory benefits (e.g., stronger slip wet skin feel in medium hard water).

U.S. Pat. No. 6,255,265 to Van Gunst is another example of reference disclosing soap, emollient and water. There is no disclosure of alkoxylated triglycerides and further no recognition that, among emollients, triglycerides retain good processability and foam. There is certainly no recognition that alkoxylated triglycerides have sensory advantages over non-alkoxylated ones. Also, the Van Gunst compositions require high level of organic electrolyte which are not so required by the subject application.

Finally, alkoxylated triglycerides are disclosed in, for example, EP 1,045,021 and EP 0,586,323, both to Kao but, in both applications, use of the alkoxylated triglycerides is in liquid compositions only. Again, as far as applicants are aware, use of such alkoxylated triglycerides at claimed levels in soap based bars is not known.

BRIEF DESCRIPTION OF THE INVENTION

Suddenly and unexpectedly, applicants have found a specific class of emollient, i.e., alkoxylated triglycerides, which can be incorporated into predominantly soap bars and which provide excellent sensory benefits (when used at claimed levels). Further, the alkoxylated triglycerides structure better than unmodified triglycerides (as measured, for example, by higher yield stress), especially at hydrophillic-lipophillic (HLB) value of greater than 10, preferably 11–24. Thus, the invention provides a simple, inexpesive method of providing excellent skin care benefits into a readily processable, simple soap bars.

More specifically, the bar compositions of the invention comprise:

(a) 50% to 90% by wt. soap;
(b) 0% to 10% by wt non-soap, non-alkoxylated triglyceride;
(c) 7% to 15%by wt. alkoxylated triglycerides; and
(d) 10% by wt. to balance water, wherein lather is at least about 60% as high relative to same base having no alkoxylated triglyceride; and wherein said bar has reduced "draggy" feel compared to identical bar comprising no alkoxylated triglyceride (as measured by expert sensory panelists trained in sensory measurements).

DETAILED DESCRIPTION OF THE INVENTION

Figure 1:
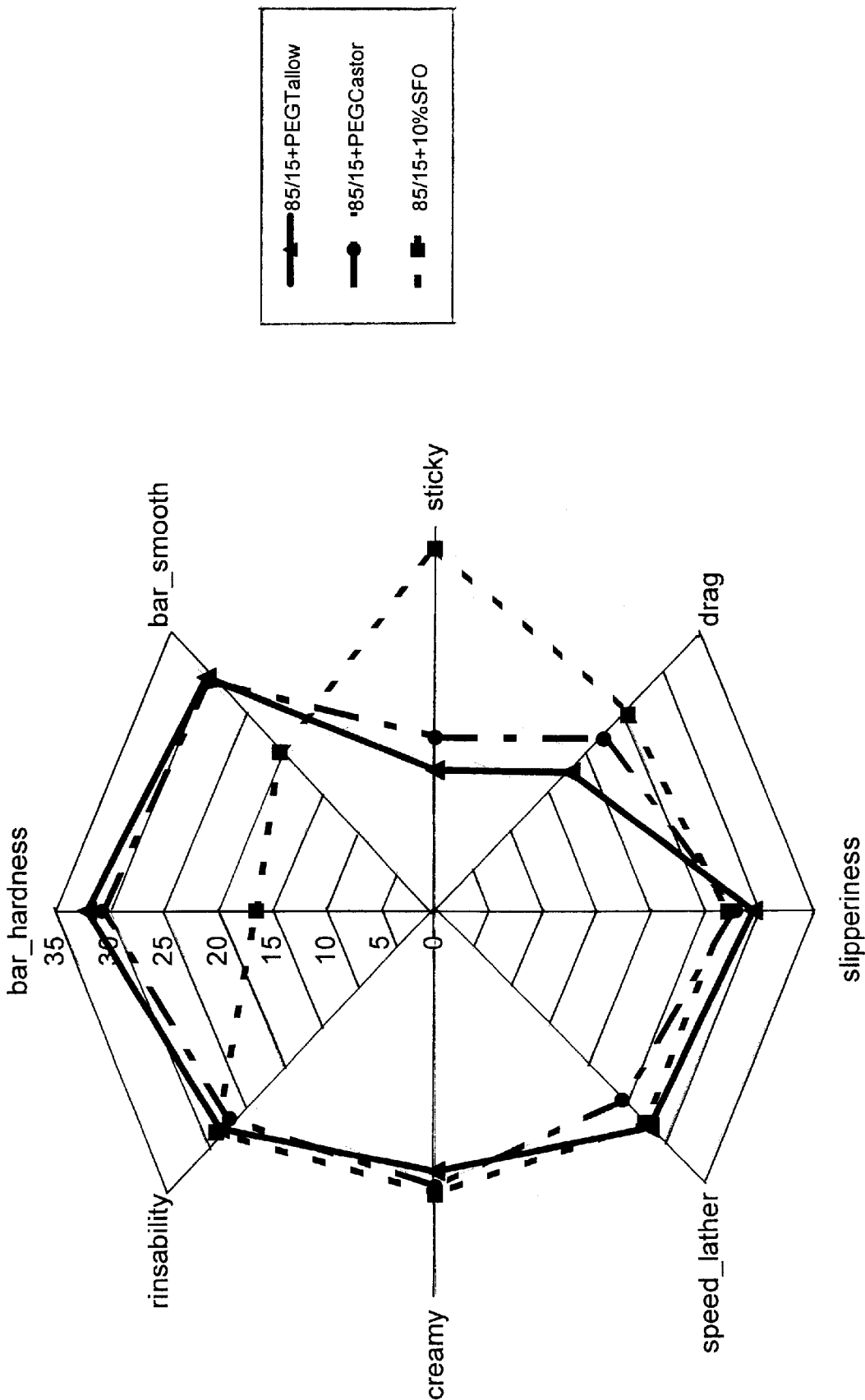
FIG. 1 shows comparison of attributes of bar with alkoxylated triglycerides (e.g., 10% by wt. alkoxylated triglyceride) compared to bar with non-alkoxylated triglyceride (10%). The further the distance from central point, the more the attribute (whether positive or negative) is perceived. As noted, the bar with alkoxylated triglyceride is far less sticky, has less drag and is perceived as more slippery (positive in this case) than bar with non-alkoxylated triglyceride. All bars are also perceived as smooth, creamy and as having good lather.

The present invention relates to compositions comprising relatively large amounts of alkoxylated triglyceride oils. The oils are generally, although not necessarily, incorporated at a point beyond the saponification stage, i.e., at finishing stage, post crystallization without at the same time hindering processing (as measured by yield stress, throughput, integrity etc.) and while retaining good lather. Moreover, the amounts provide other desirable consumer properties relative to bar without alkoxylated triglycerides and even relative to bars comprising non-alkoxylated triglycerides.

The bar composition of the invention comprises about 50 to 85%, preferably 55 to 83% by wt. soap.

The term "soap" is used herein in its popular sense, i.e., the alkali metal or alkanol ammonium salts of aliphatic, alkane-, or alkene monocarboxylic acids. Sodium, potassium, magnesium, mono-, di- and tri-ethanol ammonium cations, or combinations thereof, are suitable for purposes of this invention. In general, sodium soaps are used in the compositions of this invention, but from about 1% to about 25% of the soap may be potassium or magnesium soaps. The soaps useful herein are the well known alkali metal salts of natural of synthetic aliphatic (alkanoic or alkenoic) acids having about 8 to 22 carbon atoms, preferably about 8 to about 18 carbon atoms. They may be described as alkali metal carboxylates of acrylic hydrocarbons having about 8 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight ranges.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are C16 and higher. Preferred soap for use in the compositions of this invention has at least about 85% fatty acids having about 12 to 18 carbon atoms.

Coconut oil employed for the soap may be substituted in whole or in part by other "high-lauric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil and ucuhuba butter.

A preferred soap is a mixture of about 30% to about 40% coconut oil and about 60% to about 70% tallow. Mixtures may also contain higher amounts of tallow, for example, 15% to 20% coconut and 80% to 85% tallow.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

The bar compositions may optionally comprise 0% to 10% by wt. of optional components which are neither alkoxylated triglyceride, soap or water. If synthetic surfactant is used, it may be selected from the group consisting of anionic, nonionic, amphoteric/zwitterionic and cationic surfactants.

Anionic may be an aliphatic sulfonate (e.g., $C_8$ to $C_{22}$ alkane sulfonate or disulfonate; or aromatic sulfonate), alkyl sulfate, alkyl ether sulfate, alkyl sulfosuccinate, alkyl or acyl taurate, alkyl or acyl sarcosinates or any of the anionics described, for example, in U.S. Pat. No. 5,916,856 to Massaro et al., hereby incorporated by reference into the subject application.

Similarly amphoterics, nonionics and cationics may be any of the surfactants described in U.S. Pat. No. 5,916,856 to Massaro et al., which is hereby incorporated by reference in the subject application.

Other agents which may be used include processing aid (e.g., filler) or conditioning agents (e.g., PEG, free fatty acid or glycerin).

Other additives which may be used include one more of the following preservatives: perfumes, colors, opacifiers, optical brighteners, germicides.

The bar also comprises 10% by wt. to balance, preferably 10% to 18% by wt. water.

Finally, the compositions comprise about 7% to 15% by wt., preferably 8% to 14% by wt. alkoxylated triglyceride oil.

The triglycerides of the invention may be triesters of glycerol having a formula as follows:

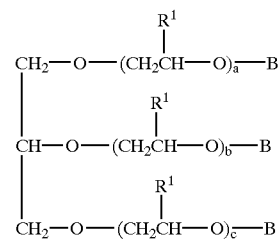

wherein $R^1$ represents H or $CH_3$, B represents H or

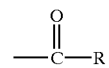

wherein R represents an alkyl, alkenyl or hydroxy alkenyl group having 6 to 22 carbon atoms, and each of a, b and c may have a value between 1 to 80, the sum of a, b and c being in the range of from 2 to 200.

In addition, triglycerides of the invention may be a mixture of mono-, di- and triesters of glycerol as described above, having a statistical distribution of the number of alkyl oxide groups per one molecule of the alkoxylated triglyceride.

Non-limiting examples of alkoxylated triglycerides include various alkoxylated castor oils (e.g., PEG 80 castor oil, PEG 30 castor oil); alkoxylated corn oil (e.g., PEG-60 corn oil), akoxylated palm kernel oil (e.g., PEG-45 PKO), and alkoxylated tallow.

Generally, the number associated with the name of compound relates to the average number of moles of alkylene oxide consumed in the reaction to form the compound.

While not wishing to be bound by theory, there also appears to be correlation between degree of alkoxylation and softness of bars, i.e., lower degree of alkoxylation appears to be associated with softer bars, and the hardness (how solid the bar is) appears to increase with degree of alkoxylation.

Preferred alkoxylated triglycerides in this regard will have hydrophilic-lipophilic balance (HLB) greater than 10, preferably 11 to 24, more preferably 12 to 20.

The alkoxylated triglycerides may be alkoxylated vegetable or fruit oils such as, for example, alkoxylated soya, cottonseed, apricot, palm, avocado, etc. or alkoxylated tallow.

The oils of the invention are preferably added in the finishing stages of soap making although it is possible to add before crystallization.

The conventional soap making process as applied to the manufacture of toilet soaps is well documented in the literature. In outline the process is as follows. In conventional 'wet' soap making, fats, i.e., tallow and coconut oil blends, are saponified in the presence of an alkali (typically NaOH) to yield fatty acids as alkaline soaps and glycerol. The glycerol is extracted with brine to give a dilute fatty acid soap solution containing around 70% soap and 30% aqueous phase. This soap solution is dried, typically by heating in heat exchangers to circa 130° C. and drying under vacuum, to a water content of around 12%, and finished by milling.

While oils may be added, as noted above, the oils of the invention, as also noted, are generally added at the finishing stage, (e.g., adding by mixing and, optionally, milling) post crystallization.

In a second embodiment of the invention, the invention comprises a process for making bars comprising soap; non-soap, non-alkoxylated triglyceride components and water in amounts noted above and wherein bar readily processable and has minimal yield stress and minimal lather volumes as also noted. Said process comprises adding 7% to 15%, preferably 8% to 14% alkoxylated triglyceride oil to the bar (generally at a finishing stage post crystallization) of the non-alkoxylated triglyceride components.

If post crystallization addition is used, it should be noted that other minors (e.g., perfume) may also be added after crystallization as long as at least sufficient components have been added (e.g., soap and structurant) to form a crystallized soap base.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES

Protocol

Yield Stress Measurement

A weighted "cheese-wire" is allowed to cut at a right angle across an edge of a soap sample, often a billet. As the wire moves into the soap so the length of wire in the soap will increase until it reaches an equilibrium position. At this point the downward force from the weight on the wire is balanced by the upward force from the viscous drag of the soap on the wire. The yield stress of the soap can be calculated from the length of the cut, the wire diameter and the applied weight. It is important that the soap temperature is also measured. For comparisons, yield stress at the measured temperature is normally converted mathematically to yield stress at a specified temperature of 40° C.

To run yield stress test, a section of stainless steel wire is attached to a counter-balanced arm which can pivot freely via a ball-race bearing. Soap billets are supported on a metal or wooden block with a V-shaped indentation.

The wire should be stainless and that the wire diameter should be measured only after the wire has been tensioned.

By applying a weight (W g) directly above the cheese wire, a constant force is exerted on the wire which will slice into the soap. The area over which the force acts increases as the depth of cut increases, and therefore the stress being exerted decreases until it is exactly balanced by the resistance of the soap and the wire stops moving. The stress at this point is equal to the yield stress of the soap. The time taken to reach this point has been found to be ~30 secs so that a standard time of 1 min is generally chosen to ensure that the yield stress has been reached. After this time the weight is removed and the length of the cut measured.

The yield stress is calculated using the semi-empirical formula:

$$\text{Yield stress} = 3/8 \frac{W \times 98.1}{1 \times d} \text{ Nm}^{-2}$$

or $$\text{Yield stress} = 0.000368 \times \frac{W}{l \times d} \text{ Nm}^{-2} \times 10^5$$

where l and d are the length of cut and diameter of the wire respectively (both measured in cm).

If the actual sample temperature is greater than 40° C. then the following equation can be used to correct the yield stress to a value of 40° C.

$$YS_{40} = YS_T \times e^b$$

Where $e = 2.718$ $$b = 16.87 \times \frac{T - 40}{273 - T}$$

Any measurement of yield stress will be highly influenced by product temperature. A good practice is to determine yield stress/temperature at the time of plodding, and again using a bar equilibrated to 40° C. in an occlusive wrapping of polythene and aluminum cooking foil.

Lather Volume Test

The amount of lather generated by a toilet soap is an important parameter affecting consumer preference. The lather volume test described here gives a measure of lather generation under standard conditions, thus allowing objective comparison of different soap formulations.

Lather is generated by trained technicians using a standardized method. The lather is collected and its volume measured. A subjective assessment of lather creaminess is made by the technicians during the generation of the lather. Typical equipment used is as follows.

Washing up bowl—1 per operator capacity 10–15 litres

Soap drainer dishes—1 per sample

Surgeons' rubber gloves—British Standard BS 4005 or equivalent range of sizes to fit all technicians Tall cylindrical glass—500–1000 ml capacity graduated in beaker or wide 10 ml intervals measuring cylinder Thermometer—Mercury types are not approved Glass rod—Sufficiently long to allow stirring in the calibrated glass beaker The procedure is typically as follows:

i. Tablet pretreatment: Wearing the specified type of glove worn inside out and well washed in plain soap, wash down all test tablets at least 10 minutes before starting the test sequence. This is best done by rotating them about 20 times through 1800 under running water;

ii. Place about 5 litres of water of known hardness and at a specified temperature (typically 20–40° C.) in a bowl. Change the water after each bar of soap has been tested;

iii. Take up the tablet, dip it in the water and remove it. Twist the tablet 15 times, between the hands, through 1800. Replace the tablet on the soap dish;

iv. The lather is generated from the soap remaining on the gloves:
   Stage 1: Rub the tips of the fingers of one hand (either hand) on the palm of the other hand 10 times;
   State 2: Grip the right hand with the left, or vice versa, and force the lather to the tips of the fingers. Repeat with the hands reversed.
This operation is repeated five times with each hand.
Repeat Stages 1 and 2;
Place the lather in the calibrated beaker.
V. Repeat the whole procedure of lather generation from paragraph iii. Twice more, combining all the lather in the beaker;
vi. Stir the combined lather gently to release large pockets of air. Read and record the volume.

The lather volume results may be assessed using a paired comparison and a value of least significant difference (LSD). Typically, six results for each bar are averaged, and paired comparisons carried out between the averaged results for each bar. If the lather volume differs by more than the LSD then the products are said to produce "significantly different amounts of lather". This LSD value is obtained from 50 separate lather assessments of standard control samples (i.e., 5 different batches: 10 samples per batch) carried out at the same temperature.

Calculations are then made as follows:
i. Calculate variance $$\sigma^2 = \frac{1}{n-1}\left[\sum x_j^2 - \frac{1}{n}\left(\sum x_j\right)^2\right]$$

ii. Look up t tables (n=50, p=0.05)
iii. Calculate the least significant difference from the equation $$L.S.D. = t\frac{2 \cdot \sigma^2}{n}$$

Expert Sensory Panel Protocol is as follows:
Expert Sensory Panel Protocol
Initial pick-up of bar (NO WATER—DRY BAR)
Evaluate: STICKINES, SMOOTHNESS & BAR HARDNESS.
TURN WATER ON
Wet hands and forearm (5 second count).
Hold bar in hands under running water (5 second count).
Out from running water (let water out from hands). Rotating soap bar 15 times.
Evaluate: SPEED OF LATHER, SLIPPERINESS & GRITTINESS
Place bar down and look at hands.
Evaluate: Amount of Bubbles & Size of Bubbles
Place forearm under water (wet wrist to elbow to avoid water on the hand).
Rub lather up onto wet forearm 10 times up and down, wrist to elbow joint (a total of 10 full counts).
Evaluate: Creaminess
Evaluate: Ease of Lather & Thickness of Lather.
Rinse hand used to apply lather (5 seconds).
Then rinse forearm under running water using rinsed hand to wipe off stroking downward 5 times under running water and evaluate: RINSABILITY
On WET SKIN out from running water
Evaluate: RESIDUE & DRAG by stroking downward 2 times.
   (With bar)
   Wet forearm (5 seconds)
   Wet bar (3 seconds)
   Rub bar onto forearm 5 times (inner forearm)
   Wet bar (3 seconds)
   Rub bar onto forearms 5 times (outer forearm)
Evaluate: Bar Hardness, Weight of Bar, Roughness, Oily Resistance (inner & outer), Speed of Lather (inner & outer) & Thickness of Lather (inner & outer)
   Blinded Procedure
   Turn water on
   Wet hands and bar (10 seconds)
   Out from water rotate bar 15 times
Evaluate: Speed of Lather, Slipperiness, Smoothness, Amount of Lather & Thickness of Lather
   Rub hands 10 times
   Rub fingertips
Evaluate: Creaminess
   Attributes are evaluated on the scale from 0 to 36 by trained panelists.

Example 1–7 and Comparative A–B

In order to show the advantages of alkoxylated triglyceride relative to both (1) base with fatty acid soap and no oil (Comparative A) and (2) base with fatty acid soap and non-alkoxylated oil (Comparative B), applicants prepared Table as noted below:

TABLE 1

Bars with 10 wt. % of Ethoxylated Triglycerides

| | Comparative A - Base; 85/15 * | Comparative B (Comparative A + 10% Sunflower) | Example 1 PEG 80 Castor Oil | Example 2 PEG 30 Castor Oil | Example 3 (PEG 30 Castor Oil) 15% | Example 4 PEG-60 Corn Oil | Example 5 PEG-45 PKO | Example 6 PEG-80 Tallow | Example 7 PEG-trioleate |
|---|---|---|---|---|---|---|---|---|---|
| HLB | — | 3.5 | 16 | 12.5 | 12.5 | 15 | 15 | 19 | 10 |
| Yield Stress | 203 | 122 | 300 | 244 | 203 | 244 | 175 | 244 | 80 |
| Yield Stress % vs. Base | 100 | 60 | 150 | 120 | 100 | 120 | 86 | 120 | 40 |
| Throughput | 145 | 192 | 118 | | | 130 | 166 | 112 | 70 |
| Lather | 50 | 50 | 45 | 40 | | 45 | 40 | 35 | 45 |
| Lather % vs. Base | 100 | 100 | 90 | 80 | | 90 | 80 | 70 | 90 |
| Comment | GP** | GP | GP | GP | P, sticky, tacky | GP | GP | GP | UP; soft, stick |

* Referring to soap base having about 85% tallow blend (predominantly $C_{16}$–$C_{18}$) and about 15% coconut blend (predominantly $C_{12}$ fatty acid soap).
**GP = Good processability; P = Marginally processable, UP = Unprocessable First, it should be noted that the number associated with name of compound represents average number of moles of ethylene oxide consumed in the reaction which forms the compounds. Further, the combination of the moles consumed and of the length of oil determine the so-called hydrophilic-lipophilic balance (e.g., the approximate ratio of hydrophilic groups to hydrophobic groups) such that those compounds having more alkoxylation and smaller hydrocarbon chain length have higher HLB.

In a preferred embodiment, the HLB should be greater than 10, preferably 11 to 24, more preferably 12 to 20. As noted, higher HLB tends to be making harder (measured by yield stress), more processable bars.

Comparing Example 2 (10% PEG-30 castor oil) to Example 3 (15% PEG-30 castor oil), it can be also be seen that about 15% is upper limit of processability.

Example 8

In order to show sensory advantage of alkoxylated oil versus non-alkoxylated oil, applicants prepared sensory evaluations as set forth in FIG. 1.

FIG. 1 shows results of the expert sensory panel evaluation of the Comparative Example B (base soap with 10% non-alkoxylated SFO—the preferred embodiment of the prior art) and examples 2 and 6 with PEG 30 castor oil and PEG 80 tallow at 10% level. Addition of ethoxylated triglycerides results in much harder and significantly smoother bars as compared to the non-ethoxylated analog. Also, bars according to the present invention are less sticky. The testing shows that new bars reduce significantly the drag wet skin feel and increase slipperiness.

What is claimed is:

1. A bar composition comprising:
   (a) 50% to 85% by wt. soap;
   (b) 0% to 10% by wt. non-soap, non-alkoxylated triglyceride;
   (c) 7% to 15% alkoxylated triglyceride; and
   (d) 10% to balance water, wherein said bar has reduced draggy feel and reduced stickiness compared to identical bar comprising no alkoxylated triglyceride.

2. A composition according to claim 1, wherein said alkoxylated triglyceride is added directly at finishing stage a post crystallization.

3. A composition according to claim 1, wherein said alkoxylated triglyceride is

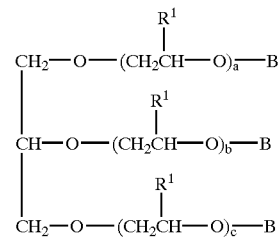

wherein $R^1$ represents H or $CH_3$, B represents H or

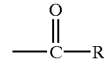

wherein R represents an alkyl, alkenyl or hydroxy alkenyl group having 6 to 22 carbon atoms, and each of a, b and c may have a value between 1 to 80, the sum of a, b and c being in the range of from 2 to 200;

or a mixture of mono-, di- and triesters of glycerol as described above.

4. A composition according to claim 1, where lather is at least 60% relative to bars having no alkoxylated triglyceride.

5. A composition according to claim 1, having 8 to 14% by weight alkoxylated triglyceride.

6. A composition according to claim 1, wherein alkoxylated triglyceride has HLB at 11–24.

* * * * *